(12) United States Patent
Tabard et al.

(10) Patent No.: US 6,310,202 B1
(45) Date of Patent: Oct. 30, 2001

(54) NITRIC OXIDE CARRIERS BASED ON POLYAZAMACROCYCLE COMPLEXES

(75) Inventors: Alain Tabard; Olivier Siri, both of Dijon; Panayotis Cocolios, Bullion; Roger Guilard, Fontaine Les Dijon, all of (FR)

(73) Assignee: L'Air Liquide, Societe Anonyme pour l'Etude Et l'Exploitation des Procedes Georges Claude, Paris, Cedex (FR)

( * ) Notice: Subject to any disclaimer, the term of this patent is extended or adjusted under 35 U.S.C. 154(b) by 0 days.

(21) Appl. No.: 09/423,363

(22) PCT Filed: Apr. 28, 1998

(86) PCT No.: PCT/FR98/00847
§ 371 Date: Jan. 11, 2000
§ 102(e) Date: Jan. 11, 2000

(87) PCT Pub. No.: WO98/50394
PCT Pub. Date: Nov. 12, 1998

(30) Foreign Application Priority Data

May 7, 1997 (FR) .................................................. 97 05674

(51) Int. Cl.⁷ ........................ C07D 255/02; C07D 257/02
(52) U.S. Cl. ............................................................. 540/465
(58) Field of Search ............................................. 540/465

(56) References Cited

PUBLICATIONS

Friederich et al, Anesth. Analg. 81(1) (1995) 152–162 (Medline abstract only).*
Sanders et al, Perfusion 15(2) (2000) 97–104 (Medline abstract only).*
Granier, C,; Guilard, R. Microchemical Journal 53 (1996) 109–121.*
Hodges, K. D.; Wollmann, R. G.; Kessel, S. L.; Hendrickson, D. N.; Van Derveer, D. G.; Barefield, E. K. Journal of the American Chemical Society 101(4) (1979) 906–917.*
Pomp, C.; Wieghardt, K. Inorganic Chemistry 27(21) (1998) 3796–3804.*
Watkins Jr., D. D.; Riley, D. P.; Stone, J. A.; Busch, D. H. Inorganic Chemistry 15(2) 1976 387–393.*

* cited by examiner

*Primary Examiner*—John M. Ford
(74) *Attorney, Agent, or Firm*—Young & Thompson

(57) ABSTRACT

Novel compounds capable of carrying and releasing nitrogen oxide (NO) in a biological medium, their use for implementing a therapeutic treatment method or a diagnostic method applied to a human or animal body, and for making medicines useful for treating or preventing disorders affecting the human or animal cardiovascular, nervous, immune, renal or pulmonary system, specifically, an organometallic complex of nitrogen oxide, wherein the cationic part is of the formula (I)

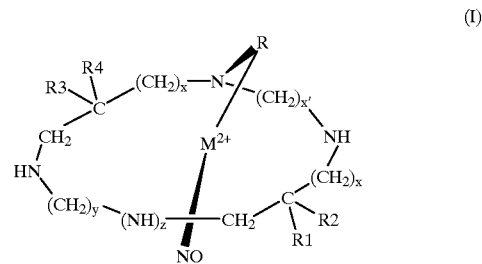

in which
x=0 or 1;
x'=2 or 3;
y=0, 2 or 3;
z=0 or 1;
with the condition that, if y=0 (or z=0) then z=0 (or y=0; respectively);
R is a group chosen from the group formed by: a hydrogen atom, $-(CH_2)_2COOH$ and

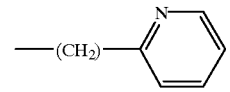

R1, R2, R3 and R4 are groups chosen from the group formed by: a hydrogen atom and alkyl groups comprising from 1 to 4 carbon atoms; and
$M^{2+}$ is a divalent cation $Fe^{++}$ or $Co^{++}$.

2 Claims, No Drawings

NITRIC OXIDE CARRIERS BASED ON POLYAZAMACROCYCLE COMPLEXES

The present invention relates to novel molecules which can convey and release nitrogen monoxide (NO) in a biological medium, to their use for carrying out a therapeutic treatment method or a diagnostic method applied to the human or animal body, as well as for the manufacture of medicinal products which can be used for treating or preventing disorders of the cardiovascular, nervous, immune, renal or pulmonary system in man or animals.

Although the nitrogen monoxide (NO) molecule has been known for a long time, its therapeutic properties have only been demonstrated since the end of the 1980s.

Thus, the first notable studies can be attributed to T. Higenbottam, who published, in "American Review of Respiratory Diseases, 1988, Volume 137", tests showing the pulmonary vasodilatory effect of NO inhaled at concentrations of about 40 ppm (parts per million by volume) and suggesting the use of inhaled NO in the therapeutic treatment of the respiratory system. However, the author comments that inhaled NO has no systemic effect, but only a local effect limited to the lungs.

Document WO-A-92/10228 pursues the previous studies and describes the use of NO gas for the preparation of medicinal products which can be administered by inhalation, for the purpose of treating or preventing reversible pulmonary bronchoconstriction or vasoconstriction in man or animals. However, the description in that document places the emphasis, on the one hand, on the unstable nature of NO which, in the presence of air, becomes oxidized very rapidly to nitrogen dioxide $NO_2$, and, on the other hand, on the toxic nature to man or animals of said $NO_2$ formed by oxidation of NO.

In order to avoid this problem of oxidation of NO in the presence of air, that document suggests coupling the NO molecule to a carrier molecule, thus allowing the NO to be conveyed to its site of use, and then releasing it thereat. Examples of such NO carriers are, in particular, S-nitrosocysteine, nitroprusside, nitrosoguanidine or azide.

In addition, the use of the NO molecule for therapeutic purposes has been the subject of many other documents, for example: WO-A-93/15779, WO-A-94/22499, WO-A-95/26768, WO-A-94/00180, WO-A-95/10315.

However, although these various publications recognize the therapeutic effects of the NO molecule, they moreover underline the persistent problem of oxidation of NO in the presence of air and the purely local, i.e. not systemic, effects of the inhaled NO molecule, i.e. the molecule administered by inhalation.

There is thus a need for molecules capable of:
combining irreversibly with the NO molecule;
conveying the NO molecule to its site of action;
releasing the NO molecule at said site of action;
avoiding the oxidation of NO in the presence of air;
being pharmaceutically acceptable.

The fact of coupling the NO molecule with such a carrier makes it possible to fully exploit the beneficial therapeutic effects of said NO molecule, without thereby running any risk of poisoning the patient with NO which has become oxidized to $NO_2$.

Currently, the only NO-carrier molecule used as a medicinal product is sodium nitroprusside. However, although this compound is of appreciable therapeutic value on account of its considerable vasodilatory activity, it has a major drawback, namely its potential toxicity resulting from the release of cyanide ions; said release of cyanide ions being due, in vivo, to a reaction of sodium nitroprusside with a reducing agent.

The result of this is that prolonged administration of such a medicinal product cannot be envisaged.

Moreover, it has been noted that the formation of cyanide ions also took place by photo-reaction. This therefore entails storing the compound and handling it under protection from light.

It is easily appreciated that such contraindications make this product relatively unappealing in therapeutic terms.

The aim of the present invention is thus to overcome the problems and drawbacks of the compounds of the prior art, by proposing novel molecules for conveying to and releasing the NO molecule at its site of use in the body, which are pharmaceutically acceptable, which are not toxic or which do not release toxic compounds, which make it possible to avoid the oxidation of NO, which are of high stability, and which are easy to synthesize, store and handle.

The invention thus relates to a molecule intended for conveying and releasing nitrogen monoxide (NO) in a biological medium, characterized in that it corresponds to formula (I) below:

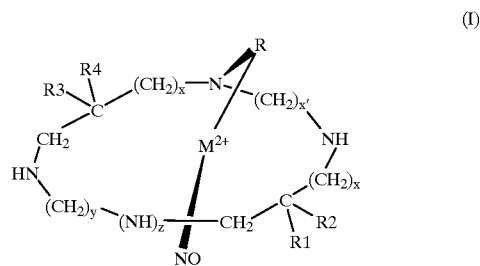

(I)

in which x=0 or 1;

x=2 or 3;

y=0, 2 or 3;

z=0 or 1;

with the condition that, if y=0 (or z=0) then z=0 (or y=0; respectively);

R is a group chosen from the group formed by: a hydrogen atom, —$(CH_2)_2COOH$ and

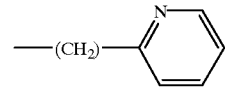

R1, R2, R3 and R4 are groups chosen from the group formed by: a hydrogen atom and alkyl groups comprising from 1 to 4 carbon atoms; and $M^{2+}$ represents a divalent cation of a metal atom.

Preferably, the divalent cation $M^{2+}$ is $Fe^{2+}$ or $Co^{2+}$.

The molecule according to the invention will advantageously be chosen from the group formed by:

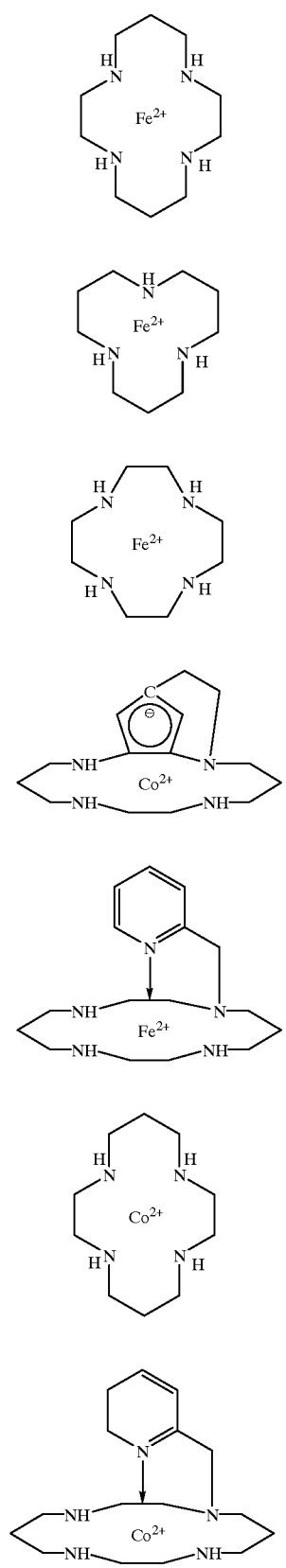

The molecules according to the invention may be used to carry out a therapeutic treatment method for the human or animal body, or to carry out a diagnostic method applied to the human or animal body.

The invention also relates to the use of one of the above molecules for the manufacture of a medicinal product which can be used for treating or preventing disorders of the cardiovascular system, the central or peripheral nervous system, the immune system, the renal system or the pulmonary system.

The present invention will now be described in greater detail with the aid of examples given for illustrative purposes, but without implying any limitation of the invention.

EXAMPLES

Examples 1 to 4 below were carried out using several NO-carrier molecules corresponding to formula (I) above. These molecules differ from each other in:

the values of x, y and z;
the nature of the electron-donating or electron-withdrawing group R;
the nature of the metal cation $M^{2+}$, i.e. $Fe^{2+}$ or $Co^{2+}$.

In all cases, the metallation reaction is carried out under inert atmosphere in order to prevent any oxidation of the metallic center ($Fe^{2+}$ or $Co^{2+}$).

Nitrosylation of the complex thus obtained is then carried out under an NO atmosphere.

In order to facilitate the reading, the following abbreviations will be used in the examples below:

333: denotes a 1,5,9-triazacyclododecane;
2222: denotes a 1,4,7,10-tetraazacyclododecane or cyclene;
2323: denotes a 1,4,8,11-tetraazacyclotetradecane or cyclam;
(2323)-(CH$_2$)$_2$—CO$_2$H: denotes an N-(2-carboxyethyl) -1,4,8,11-tetraazacyclotetradecane;
(2323)-CH$_2$—oPy: denotes an N-(2-pyridylmethyl) -1,4,8, 11-tetraazacyclotetradecane.

The nitrosyl complexes obtained are characterized by Electron Paramagnetic Resonance (EPR) spectroscopy and by Infrared (IR) spectroscopy.

EPR spectroscopy produces spectra showing an intensive signal at g=2 characteristic of a nitrosyl complex (Fe—NO) according to the nomenclature of J. H. Enemark and R. D.

Feltham (Coord. Chem. Rev., 1974, 13, 339–406), or leads to the absence of any signal, indicating the formation of a diamagnetic complex (Co—NO).

IR spectroscopy makes it possible to determine the nitrosyl complexes of bent structure (formally, coordination of NO with an electron) and those of linear structure (formally, coordination of NO with three electrons), corresponding to species: $NO^-$ or $NO^+$. Furthermore, characterization of the complex by IR spectroscopy also indicates the disappearance of the nitrosyl group coordinated to the metallic center.

The following procedures for synthesizing the nitrosyl complexes of the invention, from the various macrocycles, are detailed below in Examples 1 and 2.

Example 1

The synthesis of the iron nitrosyl complexes is carried out in the following way. $1.5 \times 10^{-4}$ mol of ligand (macrocycle) is subjected to a vacuum/argon cycle intended to remove all traces of undesirable oxygen, and is then dissolved in 10 ml of predistilled methanol under an inert atmosphere (argon). $1.5 \times 10^{-4}$ mol of iron chloride dissolved in 4 ml of methanol (step i) is added to the solution obtained. The mixture is then subjected to bubbling using NO gas for about 1 minute (step ii).

After evaporating off the solvent under reduced pressure. (about 100 Pa), the iron nitrosyl compound is recovered.

This synthesis can be represented schematically as follows:

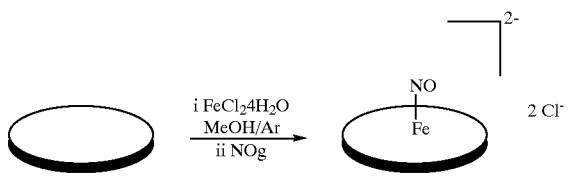

Example 2

Synthesis of the cobalt nitrosyl complexes is carried out in a similar manner to that of the iron nitrosyl complexes described in Example 1, the only difference being that a $1.5 \times 10^{-4}$ mol cobalt chloride solution is used (step i).

A cobalt nitrosyl compound is finally recovered.

This synthesis can be represented schematically as follows:

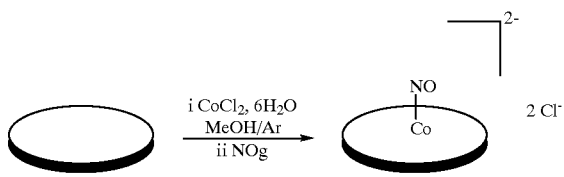

Once synthesized, these various metal nitrosyl complexes are subjected to a stability study, i.e. a study of reversibility of the nitrosylation reaction.

The reversibility of this reaction reflects the strength of the metal-NO bond, i.e. the stability of the metal nitrosyl complex, which is a function of the ligand field strength. The greater the electron density of the metal, the stronger the metal-NO bond and thus the more stable the complex.

The stability of various metal nitrosyl complexes of the invention is illustrated by Examples 3 and 4 below.

Example 3

Study of the stability of iron nitrosyl complexes.

Compound 3a: $[(2323)\text{-}(CH_2)_2\text{—}CO_2H]FeNO$

Electron Paramagnetic Resonance (EPR) spectroscopy: intense signal at g=2, characteristic of a complex (FeNO).

Compound 3b1: (333)FeNO

Infrared (IR) spectroscopy: $V_{NO}$=1810 and 1715 $cm^{-1}$

EPR spectroscopy: intense signal at g=2.

Compound 3b2: (2222)FeNO

IR spectroscopy: $V_{NO}$=1740 $cm^{-1}$, characteristic of an $NO^+$ species.

EPR spectroscopy: intense signal at g=2.

Compound 3c1: (2323)FeNO

IR spectroscopy: $V_{NO}$=1720 and 1610 $cm^{-1}$, characteristic of an $NO^+$ species.

EPR spectroscopy: intense signal at g=2.

Compound 3c2: $[(2323)\text{-}CH_2\text{—}oPy]FeNO$

IR spectroscopy: $V_{NO}$=1640 $cm^{-1}$, characteristic of an $NO^+$ species.

EPR spectroscopy: intense signal at g=2.

Compound 3d: [18ane]N4FeNO

IR spectroscopy: $V_{NO}$=1777 and 1714 $cm^{-1}$, characteristic of $NO^+$ species.

EPR spectroscopy: intense signal at g=2.

Compound 3d corresponds to the molecule (X) represented above, in which the groups $R_1$, $R_2$, $R_3$ and $R_4$ are methyl groups.

The presence of an electron-withdrawing propionate group in a trans position relative to the nitrosyl ligand (compound 3a) weakens the Fe-NO bond between the iron and the NO molecule. Accordingly, compound 3a was found to be moderately stable and could not be isolated in the absence of NO.

Only the compounds 3b1, 3b2 and 3d were found to be good NO carriers. On the other hand, compounds 3c1 and 3c2 release NO with greater difficulty since the Fe-NO bond is stronger (the ligand field strength is thus greater); they undergo an oxidation of the equatorial ligand and of the axial ligand NO into $NO_2$. However, their use as carriers should not be excluded, given that the release of NO from nitro derivatives is possible.

Example 4

Study of the stability of cobalt nitrosyl complexes.

Compound 4a1: $[(2323)\text{-}(CH_2)_2\text{—}CO_2H]CoNO$

IR spectroscopy: $V_{NO}$=1380 $cm^{-1}$, characteristic of an $NO^-$ species.

EPR spectroscopy: no EPR signal observed, in accordance with a diamagnetic nitrosyl complex (CoNO).

Compound 4a2: $[(2323)\text{-}(CH_2)_2\text{—}oPy]CoNO$

IR spectroscopy: $V_{NO}$=1380 $cm^{-1}$, characteristic of an $NO^-$ species.

EPR spectroscopy: no EPR signal observed. Diamagnetic compound characteristic of a nitrosyl complex (CoNO).

Compound 4b: (2323)CoNO

IR spectroscopy: $V_{NO}$=1605 $cm^{-1}$, characteristic of an $NO^-$ species.

EPR spectroscopy: no EPR signal observed. Diamagnetic compound characteristic of a nitrosyl complex (CONO).

Compounds 4a1 and 4a2 bind NO reversibly; a dissociation is observed under inert atmosphere (argon).

On the other hand, compound 4b shows no reversibility of binding.

In summary, the synthesis and physicochemical study of the compounds of the invention have made it possible to demonstrate extensive reactivity of these compounds with respect to NO, i.e. not only their capacity to bind the NO molecule, but also their ability to release it subsequently.

The compounds of the invention are thus capable of being used, as therapeutic agents, for the purpose of conveying and releasing in vivo the NO molecule which they bind reversibly.

What is claimed is:

1. An organometallic complex of nitrogen oxide that can convey and release nitrogen monoxide in a biological medium, wherein the cationic part is of the formula (I)

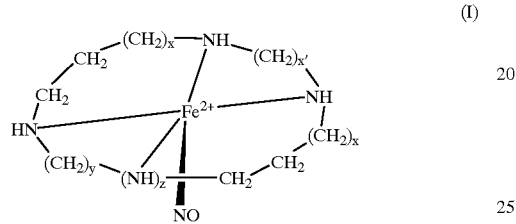

(I)

in which
x=0 or 1;
x'=2 or 3;
y=0, 2 or 3;
z=0 or 1;
with the condition that, if y=0 (or z=0) then z=0 (or y=0; respectively).

2. An organometallic complex according to claim 1, wherein the organometallic part of the cation linked to nitrogen oxide by the iron atom is selected from the group consisting of

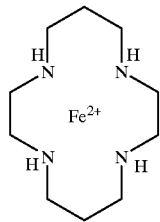

(II)

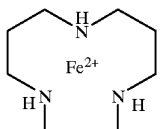

(III)

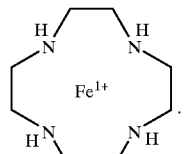

(IV)

* * * * *